United States Patent [19]

Kan et al.

[11] Patent Number: 4,895,801
[45] Date of Patent: Jan. 23, 1990

[54] METHOD FOR PRODUCING OLIGOSACCHARIDES

[75] Inventors: Tatsuhiko Kan; Tsuneo Terashima; Yoichi Kobayashi, all of Tokyo, Japan

[73] Assignee: Kabushiki Kaisha Yakult Honsha, Tokyo, Japan

[21] Appl. No.: 103,416

[22] Filed: Oct. 1, 1987

[30] Foreign Application Priority Data

Oct. 7, 1986 [JP] Japan ................................ 61-237075

[51] Int. Cl.$^4$ ......................... C12P 19/04; C12R 1/69
[52] U.S. Cl. .................................. 435/101; 435/175; 435/207; 435/918
[58] Field of Search ................ 435/42, 101, 175, 207, 435/208, 822, 918

[56] References Cited

U.S. PATENT DOCUMENTS 4,435,389  3/1984  Mutai et al. ..................... 435/244

OTHER PUBLICATIONS

Derwent Abs. 88-169362/25 EP-272095 (6-1988) Yakult.
Derwent Abs. 88-121248/18, EP-266177 (5-1988) Yakult.
Derwent Abs. 87-215440/31, FR2591484 (6-1987) Snow.
Derwent Abs. 87-202530/29, J62130695 (6-1987) Nisshin.
Derwent Abs. 87-189055/27, J62118886 (5-1987) Daiwa.
Derwent Abs. 87-181811/26, J62111685 (5-1987) Nisshin.
Derwent Abs. 87-033274/05, J62128956 (12-1986) Nisshin.
Derwent Abs. 85-090879/15, J60041449 (3-1985) Yakult.
Derwent Abs. 83-841881/50, (J58190388) 11-83, Yakult.
Biotech 87-06389, Prakash et al., Biotech Lett. (1987) 9,4,249.52.
Japio Abs. 86-289856, (J61289856), 12-86, Nisshin Seito.
Biotech. Abs. 84-1956 (J58190388), Yakult, 11-1983.
Japio Abs. 83-099497 (J58099497), 6-83, Snow.
Biotech Abs. 88-02154 (Biotech. Bioeng.) (1987, 30, 9, 1026-3).

*Primary Examiner*—Herbert J. Lilling
*Attorney, Agent, or Firm*—Oblon, Spivak, McClelland, Maier & Neustadt

[57] ABSTRACT

A method for producing oligosaccharides which are represented by the general formula Gal-(Gal)n-Glc (where Gal is a galactose residue, Glc is a glucose residue, and n is an integer from 1 to 4) which is characterized in that lactose or a lactose-containing substance is treated with at least two kinds of $\beta$-galactosidases which are produced by different microorganisms. The present invention provides a method of producing oligosaccharides to obtain sweet saccharide mixture which provide sweetness and add oligosaccharides to food and drinks, with a lower increase in calories than that of conventional additives.

3 Claims, No Drawings

METHOD FOR PRODUCING OLIGOSACCHARIDES

BACKGROUND OF THE INVENTION

This invention relates to a method for producing oligosaccharides which are proliferation accelerating factors for bifidobacteria.

In particular, this invention provides a method for producing oligosaccharides for obtaining a sweet saccharide mixture which contains an appropriate balance of monosaccharides useful as sweeteners, and a minimum of unwanted disaccharides, and can provide sweetness and add oligosaccharides to food and drinks with a lower increase in calories than that of conventional additives.

In recent years, it has become evident that the glucose/galactose series oligosaccharides produced from a $\beta$-galactosyl transfer reaction of lactose are the main constituents of breast milk oligosaccharides, and act as a proliferation accelerating factor &or bifidobacteria in human intestines (Japanese Patent Publication No 58-20266, etc.).

The oligosaccharides represented by the general formula Gal-(Gal)n-Glc (where Gal is a galactose residue, Glc is a glucose residue and n is an integer from 1 to 4, hereinafter referred to simply as oligosaccharides) have been widely used in a variety of fields, for example, as additives to fermented milk and powdered milk for infants.

A method in which lactose is treated with a $\beta$-galactosidase from Aspergillus oryzae (Japanese Patent Publication No. 58-20266) is a typical method for producing oligosaccharides, but the reaction product obtained in the above-described enzyme treatment is saccharide mixture containing disaccharides (mainly unreacted lactose) and monosaccharides (galactose and glucose), in addition to oligosaccharides. The reaction products are ordinarily used as they are, since no method of economically obtaining just oligosaccharides from the mixture has yet been developed, and the sweetness of the monosaccharides can often be advantageously utilized.

Although the above-described conventional production method which uses a $\beta$-galactosidase produced by Aspergillus oryzae provides a high yield of oligosaccharides in a shorter time than that when the $\beta$-galactosidase is produced by other microorganisms, this method has a disadvantage in that it remains large quantities of disaccharides, mainly unreacted lactose. These disaccharides have almost no sweetness and so can not be used as a source of sweetness, and from the aspect of lactose intolerance, it is desirable to have as little lactose as possible in the final product.

A reaction product having a lower amount of disaccharides can be obtained from a $\beta$-galactosidase with a longer treatment time, but a noticiable reduction in the yield of oligosaccharides cannot be avoided in such a case.

Therefore, when heretofore conventional oligosaccharides are to be added to food and drink, a product which has high oligosaccharide content and thus contains a great deal of disaccharides but a relatively small amount of monosaccharides is commonly used. Further, a sweetener such as sucrose cane sugar) or liquid sugar is also added if the food or drink needs more sweetness, so the resultant food or drink is high in calories because of its exceedingly high saccharide content.

The purpose of the present invention is to solve the above-described problems in the utilization of oligosaccharides.

SUMMARY OF THE INVENTION

The present invention is designed to provide a method for producing oligosaccharides for obtaining a sweet saccharide mixture having appropriate amount of monosaccharides useful as sweeteners with a minimum of unwanted disaccharides. The saccharide mixture can provide sweetness and the addition of oligosaccharides to food and drink with less of an increase in calories than that of conventional additives.

Another purpose of the present invention is to provide a method in which lactose is converted into oligosaccharides by the treatment of a lactose-containing substance, such as milk, with a $\beta$-galactosidase, so that, even if these oligosaccharides are utilized as food or drink, the quantity of undesirable disaccharides therein can be reduced to a minimum.

Further, in order to achieve these purposes, the present invention provides a method for producing oligosaccharides represented by a general formula Gal-(Gal)n-Glc (where Gal is a galactose residue, Glc is a glucose residue, and n is an integer from 1 to 4), characterized in that lactose or a lactose-containing substance is treated with at least two kinds of $\beta$-galactosidases produced by different microorganisms.

DETAILED DESCRIPTION OF THE PREFERRED EMBODIMENTS

The present invention is characterized by treating lactose or a lactose-containing substance with at least two kinds of $\beta$-galactosidases produced by different microorganisms.

In this production method, the saccharide balance in the final product is greatly improved, since the quantitY of residual lactose can be reduced without reducing the yield of oligosaccharides, although the reason for this is not clear.

In the conventional method in which oligosaccharides are produced by reacting one kind of $\beta$-galactosidase with lactose, products containing large quantities of disaccharides, such as those from unreacted lactose, are produced, even if the Yield of oligosaccharides is high, and economical separation of the products is difficult, forming an obstacle to their use. In the present invention in which two kinds of $\beta$-galactosidases are used, the yield of oligosaccharides is improved, exceeding the limit of conventional methods, and further, the yield of monosaccharides is increased while the amount of disaccharides is decreased remarkably. This effect is particularly conspicuous when a $\beta$-galactosidase produced by Aspergillus oryzae is used in a first treatment (see Examples 1~3 below). Therefore, in the present invention, a saccharide mixture containing large proportions of oligosaccharides which are useful as a bifidobacterium proliferation accelerating factor and monosaccharides which are useful as sweeteners can be efficiently obtained, and the superior characteristics of oligosaccharides can be widely utilized without having to worry about any calorie increase or lactose intolerance.

As is well known, $\beta$-galactosidases can be produced by a variety of molds, bacteria, or yeasts, but all combinations of these microorganisms are permitted in the present invention, so long as the microorganisms are suitable for the production of food. However, with β-galactosidases produced by different microorganisms, it is desirable to adopt a combination with enzyme properties which are as different as possible, such as a combination of β-galactosidases produced by mold and yeast.

The β-galactosidases which can be used in the production method according to the present invention are the substances produced with the aid of the following microorganisms:

Molds:
*Aspergillus oryzae, Aspergillus niger, Aspergillus flavus, Mucor pusillus.*

Bacteria:
*Streptococcus thermophilus, Streptococcus lactis, Lactobacillus bulgaricus, Lactobacillus salivarius, Lactobacillus leichimanni, Lactobacillus helveticus, Bacillus stearothermophilus, Bacillus brevis, Thermus thermophilus, Bifidobacterium bifidum, Bifidobacterium longum, Bifidobacterium breve, Bifidobacterium adolescentis.*

Yeasts:
*Kluyveromyces fragilis, Kluyveromyces lactis, Candida pseudotropicalis.*

Although, in the present invention, the reaction can be completed in one treatment by mixture of two kinds of β-galactosidases, successive treatments in which a treatment by one β-galactosidase is performed, and, after the enzyme has been made inactive, a treatment by another β-galactosidase is performed is advantageous in that the reaction can be easily controlled, and a superior processing effect can be obtained. In either case, one or both of two kinds of β-galactosidases can be used in the form of immobilized enzymes.

The conventional method can be adopted for the method for treating lactose or a lactose-containing substance by β-galactosidase. In other words, a lactose-containing substance, such as lactose itself, milk, or whey, is treated at a lactose concentration of 10~50 weight %, an enzyme concentration of 1~100 units/ml, and at a condition close to an optimum pH and temperature for the enzyme used. Although the concentration of monosaccharides, such as glucose and galactose, and oligosaccharides increase virtually linearly as the reaction proceeds at first, slightly more complicated changes appear in subsequent reactions, so the oligosaccharides gradually decrease after a certain time. In the initial enzyme treatment in the successive treatments, or in the mixed treatment, the reaction time is desirably set to the time required for obtaining the highest yield of oligosaccharides or the time at which the ratio of oligosaccharides to disaccharides is at a maximum. After the initial enzyme treatment is completed in the successive treatments, the enzyme is inactivated by heating, and the next enzyme treatment is performed. Since, in the second enzyme treatment, the quantities of disaccharides decreases particularly remarkably, and the oligosaccharides increase or reduce according to differences in the treatment conditions such as the origin of the enzyme used and the reaction temperature, the reaction can be stopped at a suitable stage, taking into account the balance between oligosaccharides and monosaccharides required for the product.

The reaction products can be used as they are or after decoloring, purification, concentration, drying or other processing necessary for the formation of food or drink, and can be used as sweet saccharide mixtures or as food or drink which possess the bifidobacterium proliferation accelarating effect. Of course, the reaction product can be utilized for the production of purified oligosaccharides, and the oligosaccharides of a high purity can be easily obtained, since the quantity of disaccharides is small.

Hereinafter, the present invention is illustrated by examples and comparison examples.

EXAMPLE 1

40 kg of lactose was dissolved in hot water to form a total quantity of 80 l and 800,000 units of β-galactosidases produced by *Aspergillus oryzae* (Lactase Y-400, KK Yakult Honsha) were added to the lactose. Then both substances were reacted at 50° C., at a pH of 6.5, for 5 hours. The enzyme was then made inactive by heating the reaction liquid to obtain light yellow primary reaction liquid.

Then 1 l of the primary reaction liquid was taken and 10 ml of 1M-potassium phosphate buffer solution (pH 6.7) and 1,500 units of β-galactosidase (Lactozyme, Novo Co) produced by *kluyveromyces fragilis* were added to the primary reaction liquid, and the reaction continued at 40° C. for 16 hours. The enzyme was made inactive by heating the reaction liquid, and the product was decolored by 50 g of active carbon to obtain a colorless transparent saccharide solution.

EXAMPLE 2

1 l of the primary reaction liquid of Example 1 wa secondarily-treated by β-galactosidase produced by *Streptococcus thermophilus* to obtain a transparent saccharide solution.

EXAMPLE 3

1 l of the primary reaction liquid of Example 1 was secondarily-treated by β-galactosidase produced by *Lactobacillus bulgaricus* to obtain a transparent saccharide solution.

EXAMPLE 4

10 kg of lactose was dissolved in hot water to form a total quantity of 20 l and 200 ml of 1M-potassium phosphate buffer solution (pH 6.7) and 100,000 units of β-galactosidase produced by *KluyveromYces fragilis* were added to the lactose, then these substances were reacted at 40 ° C. for 4 hours. The enzyme was made inactive by heating the reaction liquid to make a light yellow primary reaction liquid. 1 l of the primary reaction liquid was secondarily-treated by β-galactosidase produced by *Aspergillus oryzae* to obtain a transparent saccharide solution.

EXAMPLE 5

1 l of the primary reaction liquid of Example 4 was secondarily-treated by β-galactosidase produced by *Streptococcus thermophilus* to obtain a transparent saccharide solution.

EXAMPLE 6

1 l of the primary reaction liquid of Example 4 was secondarily-treated by β-galactosidase produced by *Lactobacillus bulgaricus* to obtain a transparent saccharide solution.

EXAMPLE 7

10 kg of lactose was dissolved in hot water to form a total quantity of 20 l and 200 ml of 1M-potassium phosphate buffer solution (pH 6.7) and 300,000 units of β- galactosidase produced by *Streptococcus thermophilus* were added, and the substance was reacted at 40° C. for 16 hours. The enzyme was made inactive by heating the reaction liquid to obtain light yellow primary liquid.

Then 1 l of the primary reaction liquid was taken and was secondarily-treated by the β-galactosidase produced by *Aspergillus oryzae* to obtain a transparent saccharide solution.

EXAMPLE 8

1 l of the primary reaction liquid of Example 7 was secondarily-treated by β-galactosidase produced by *Kluyveromyces fragilis* to obtain a transparent saccharide solution.

EXAMPLE 9

1 l of the primary reaction liquid of Example 7 was secondarily-treated by β-galactosidase produced by *Lactobacillus bulgaricus* to obtain a transparent saccharide solution.

EXAMPLE 10

10 l of lactose was dissolved in hot water to form a total quantity of 20 l and 200 ml of 1M-potassium phosphate buffer solution (pH 6.7) and 30,000 units of galactosidase produced by *Lactobacillus bulgaricus* was added, and the substance was reacted at 40° C. for 16 hours. The enzyme was made inactive by heating the reaction liquid, and a light yellow primary reaction liquid was obtained.

Then, 1 l of the reaction liquid was taken and was secondarily-treated by β-galactosidase produced by *Aspergillus oryzae* to obtain a transparent saccharide solution.

EXAMPLE 11

1 l of the primary reaction liquid of Example 10 was secondarily-treated by β-galactosidase produced by *Kluyveromyces fragilis* to obtain a transparent saccharide solution.

EXAMPLE 12

1 l of the primary reaction liquid of Example 10 was secondarily-treated by β-galactosidase produced by *Streptococcus thermophilus* to obtain a transparent saccharides solution.

The degree of sweetness was evaluated by preparing a sample of each test liquid adjusted to Brix 10 and cane sugar liquids of Brix 2 to 10, and having ten experienced panellists judge the range of values of concentration at which sweetness equal to that of the test liquid was obtained. A result was expressed as a value relative to a degree of sweetness of cane sugar of 100.

The results of the saccharide solutions in each example and the composition of its saccharides are summarized in Table 1. In the Table the contents of the comparison examples are as follows:

Comparison example 1: primary reaction liquid of Example 1
Comparison example 2: primary reaction liquid of Example 4
Comparison example 3: primary reaction liquid of Example 7
Comparison example 4: primary reaction liquid of Example 10

In each of these comparison examples (primary reaction liquid in each example), treatment is performed for the reaction time necessary for obtaining the highest yield of oligosaccharides, which was confirmed by preparatory experiments for the β-galactosidases used for the processing.

TABLE 1

| Example | oligo-saccharides (O)wt % | di-saccharides (D)wt % | mono-saccharides (M)wt % | O/D | degree of sweetness |
|---|---|---|---|---|---|
| 1 | 27 | 17 | 56 | 1.59 | 45 |
| 2 | 38 | 26 | 36 | 1.46 | 35 |
| 3 | 38 | 27 | 35 | 1,41 | 35 |
| 4 | 16 | 38 | 46 | 0.42 | 40 |
| 5 | 20 | 31 | 49 | 0.65 | 40 |
| 6 | 17 | 29 | 54 | 0.59 | 45 |
| 7 | 21 | 34 | 45 | 0.62 | 40 |
| 8 | 27 | 21 | 52 | 1.29 | 40 |
| 9 | 29 | 34 | 37 | 0.85 | 35 |
| 10 | 21 | 32 | 47 | 0.66 | 40 |
| 11 | 27 | 25 | 48 | 1.08 | 50 |
| 12 | 30 | 31 | 39 | 0.98 | 35 |
| Comparative Example | | | | | |
| 1 | 27 | 50 | 23 | 0.54 | 25 |
| 2 | 10 | 55 | 35 | 0.18 | 35 |
| 3 | 26 | 52 | 22 | 0.50 | 30 |
| 4 | 28 | 48 | 24 | 0.58 | 30 |

EXAMPLE 13

36 kg of powdered skimmed milk was dissolved in warm water to form a total quantity of 100 l and 1,000,000 units of β-galactosidase produced by *Aspergillus oryzae* was added to the milk. The mixture was reacted at 60° C. for 1 hour, and the enzyme was made inactive by heating at 80° C. for 2 hours. The reaction liquid was kept at 60° C., and 500,000 units of β-galactosidase produced by *Lactobacillus bulgaricus* was added and reacted for 2 hours. Finally, 300 l of water at 90° C. was added to dilute the mixture, and, at the same time, to make he enzyme inactive and obtain an oligosaccharides-containing processed milk which contained a low level of lactose but which was sweet. The saccharide content of this milk was as follows: 1.35 % oligosaccharides, 1.40 % disaccharides, and 1.76 % monosaccharides.

What is claimed is:

1. A method for producing oligosaccharides which are represented by the general formula Gal-(Gal)$_n$-Glc, where Gal is a galactose residue, Glc is a glucose residue, and n is an integer of from 1 to 4, characterized in that lactose or a lactose-containing substance is treated with at least two kinds of beta-galactosidases produced by different microorganisms.

2. The method of claim 1, comprising using successive treatments by two kinds of beta-galactosidases produced by different microorganisms.

3. The method of claim 2, wherein beta-galactosidase produced by *Aspergillus oryzae* is used in the first treatment.

* * * * *

UNITED STATES PATENT AND TRADEMARK OFFICE
CERTIFICATE OF CORRECTION

PATENT NO. :    4,895,801

DATED      :    Jan. 23, 1990

INVENTOR(S) :   Yoichi Kobayashi, et al

It is certified that error appears in the above-identified patent and that said Letters Patent is hereby corrected as shown below:

In the header information on the Title Page,
"Kan et al." should be --Kobayashi et al.--

The entry for "[75] Inventors:" should read
--Yoichi Kobayashi; Tatsuhiko Kan; Tsuneo Terashima,
  all of Tokyo, Japan--

Signed and Sealed this

Nineteenth Day of March, 1991

*Attest:*

HARRY F. MANBECK, JR.

*Attesting Officer*  *Commissioner of Patents and Trademarks*